(12) United States Patent
Rohl et al.

(10) Patent No.: US 11,389,633 B2
(45) Date of Patent: Jul. 19, 2022

(54) VASCULAR INTRODUCER HUBS FOR REDUCING BLOOD LEAKAGE

(71) Applicants: BOSTON SCIENTIFIC SCIMED, INC., Maple Grove, MN (US); MAYO FOUNDATION FOR MEDICAL EDUCATION AND RESEARCH, Rochester, MN (US)

(72) Inventors: James P. Rohl, Prescott, WI (US); James K. Cawthra, Jr., Ramsey, MN (US); Benn Horrisberger, Blaine, MN (US); James A. Klos, Bay City, WI (US); David J. Lehse, Oakdale, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 959 days.

(21) Appl. No.: 16/312,278

(22) PCT Filed: Dec. 16, 2016

(86) PCT No.: PCT/US2016/067228
§ 371 (c)(1),
(2) Date: Dec. 20, 2018

(87) PCT Pub. No.: WO2017/106681
PCT Pub. Date: Jun. 22, 2017

(65) Prior Publication Data
US 2019/0160276 A1 May 30, 2019

Related U.S. Application Data

(60) Provisional application No. 62/269,700, filed on Dec. 18, 2015.

(51) Int. Cl.
*A61M 39/10* (2006.01)
*A61M 25/00* (2006.01)
(Continued)

(52) U.S. Cl.
CPC .... *A61M 39/1011* (2013.01); *A61M 25/0097* (2013.01); *A61M 39/10* (2013.01); *A61L 29/02* (2013.01); *A61L 29/14* (2013.01)

(58) Field of Classification Search
CPC .... A61L 29/02; A61L 29/14; A61M 25/0097; A61M 39/10; A61M 39/1011;
(Continued)

(56) References Cited

U.S. PATENT DOCUMENTS

| 5,599,327 A | 2/1997 | Sugahara et al. |
| 5,738,664 A | 4/1998 | Erskine et al. |
| 5,911,710 A * | 6/1999 | Barry ............... A61M 39/0693 604/249 |

(Continued)

FOREIGN PATENT DOCUMENTS

| CN | 204246678 U | 4/2015 |
| CN | 104800954 A | 7/2015 |

(Continued)

OTHER PUBLICATIONS

International Search Report and Written Opinion dated Jun. 8, 2017 for International Application No. PCT/US2016/067228.

(Continued)

*Primary Examiner* — Jason E Flick
(74) *Attorney, Agent, or Firm* — Seager, Tufte & Wickhem, LLP (57) ABSTRACT

A vascular introducer hub has a body that includes a proximal end, a distal end, and a lumen defined therethrough. The hub includes first and second seals disposed within the body. The first seal includes a first polymeric material and the second seal includes a second polymeric material. The hub is characterized by the first and second polymeric materials having different durometers.

17 Claims, 6 Drawing Sheets

(51) Int. Cl.
*A61L 29/02* (2006.01)
*A61L 29/14* (2006.01)

(58) Field of Classification Search
CPC ...... A61M 39/1055; A61M 2039/1072; A61M 39/22; A61M 2039/2433; A61M 25/00
See application file for complete search history.

(56) References Cited

U.S. PATENT DOCUMENTS

| | | | |
|---|---|---|---|
| 2005/0113805 A1* | 5/2005 | Devellian | A61M 25/0075 604/539 |
| 2008/0097386 A1* | 4/2008 | Osypka | A61M 39/0613 604/510 |
| 2011/0166527 A1* | 7/2011 | Wells | A61B 17/3498 604/167.05 |
| 2015/0305863 A1* | 10/2015 | Gray | A61F 2/2436 623/2.11 |

FOREIGN PATENT DOCUMENTS

| | | |
|---|---|---|
| EP | 0832665 A2 | 4/1998 |
| EP | 2044898 A1 | 4/2009 |
| JP | H07163666 A | 6/1995 |
| JP | H10108911 A | 4/1998 |
| JP | H114894 A | 1/1999 |
| JP | 2000279534 A | 10/2000 |
| JP | 2000316986 A | 11/2000 |
| JP | 2002017865 A | 1/2002 |
| JP | 2003154009 A | 5/2003 |
| JP | 2013176505 A | 9/2013 |
| WO | 2015168006 A1 | 11/2015 |

OTHER PUBLICATIONS

International Preliminary Report on Patentability dated Jun. 28, 2018 for International Application No. PCT/US2016/067228.

* cited by examiner

VASCULAR INTRODUCER HUBS FOR REDUCING BLOOD LEAKAGE

CROSS-REFERENCE TO RELATED APPLICATIONS

This application is a National Stage of International Application No. PCT/US2016/067228, filed Dec. 16, 2016, which claims the benefit of priority under 35 U.S.C. § 119 of U.S. Provisional Application Ser. No. 62/269,700, filed Dec. 18, 2015, the entire disclosures of which are incorporated herein by reference.

TECHNICAL FIELD

The present invention relates to devices and methods that include vascular introducer hubs.

BACKGROUND

Vascular introducer hubs can be used in minimally invasive procedures that involve repeated introduction and removal of catheters and guidewire within a vascular system of a patient. The introducer hubs can also allow for the repositioning of the catheter or guidewire during a procedure, but often this requires the opening of a valve within the hub that permits bodily fluids, such as blood, from leaking out through the hub. When the valve is close to prevent blood leakage, however, the catheter or guidewire is prevented from being repositioned. There is a need for vascular introducer hubs that can minimize blood leakage such that devices received into the introducer hub can be repositioned or manipulated without a significant loss of bodily fluids.

SUMMARY

This document relates to devices and methods that include vascular introducer hubs. Disclosed herein are various embodiments of vascular introducer hubs for allowing devices to pass therethrough while minimizing blood leakage during a medical procedure.

In Example 1, a vascular introducer hub includes a body, and first and second seals disposed within the body. The body includes a proximal end, a distal end, and a lumen defined therethrough. The first seal includes a first polymeric material and the second seal includes a second polymeric material. The hub includes first and second polymeric materials having different durometers (hardness).

In Example 2, the vascular introducer hub of Example 1, wherein the first polymeric material has a lower durometer than the second material.

In Example 3, the vascular introducer hub of Example 2, wherein the first seal comprises a silicone having a durometer ranging from about 30 Shore A to about 40 Shore A and the second seal comprising a silicone material having a durometer ranging from about 40 Shore A to about 60 Shore A.

In Example 4, the vascular introducer hub of any one of Examples 1-3, further including a first seal actuator rotatably coupled to the body and located adjacent to the first seal and a second seal actuator rotatably coupled to the body and located adjacent to the second seal, wherein the first seal actuator is configured to compress the first seal when actuated and the second seal actuator is configured to compress the second seal when actuated.

In Example 5, the vascular introducer hub of Example 4, wherein the first seal includes a seal body defining a first lumen therethrough with a reduceable inner diameter configured to reduce in diameter when the seal body is compressed by the first seal actuator.

In Example 6, the vascular introducer hub of any one of Examples 1-5, wherein the first and second seals, when each are in a non-compressed state, include lumens sized to receive a catheter device having a diameter ranging from about (0.105 inches, or 8 French) to about 0.341 inches (26 French).

In Example 7, the vascular introducer hub of any one of Examples 1-6, wherein the first seal is configured to allow a device to move distally or proximally along a longitudinal axis defined by the body when the first seal is in a partially closed state and in a fully closed state.

In Example 8, the vascular introducer hub of any one of Examples 1-7, wherein the second seal is configured to form a fluid-tight seal around a device when the second seal is compressed partially and prevents a device to move distally or proximally along a longitudinal axis defined by the body when the second seal is in a fully closed state.

In Example 9, the vascular introducer hub of any one of Examples 1-8, wherein the body of the hub defines a chamber between the first and second seals, the chamber being in fluid communication with the lumen of the body.

In Example 10, the vascular introducer hub of Example 9, further including a venting element coupled to the body and in fluid communication with the chamber, the venting element configured to release gases from the chamber while leaving liquids in the chamber.

In Example 11, the vascular introducer hub of Example 10, wherein the venting element extends in radial direction relative to a longitudinal axis defined by the body.

In Example 12, the vascular introducer hub of Example 9 or Example 10, wherein the venting element including a gas permeable filter made of a porous or microporous membrane made of materials such as, but not limited to, polypropylene, polyethylene, polytetrafluoroethylene, other polyolefin, polyester, or combinations thereof.

In Example 13, the vascular introducer hub of any one of Examples 1-12, further including a third seal located distal to the second seal.

In Example 14, a vascular introducer device includes an elongate shaft and a hub. The elongate shaft includes a proximal end, a distal end, and a lumen therethrough. The lumen is sized to receive a catheter device. The distal end defines an opening configured to allow the catheter device to pass through. The hub is coupled to the proximal end of the elongate shaft. The hub includes a body and first and second seals disposed within the body. The body includes a proximal end, a distal end, and a lumen defined therethrough. The first and second seals are disposed within the body. The first seal includes a first polymeric material and the second seal including a second polymeric material. The hub may be characterized by the first and second polymeric materials having different durometers.

In Example 15, the vascular introducer device of Example 14, wherein the first seal defines a first seal lumen and comprises a seal body that includes a frustoconical distal portion tapered in a distal direction and being configured for puckering inwardly when the first seal is compressed, and wherein the second seal defines a second seal lumen and comprises a seal body that includes a frustoconical distal portion tapered in a distal direction and being configured for puckering inwardly when the second seal is compressed.

In Example 16, the vascular introducer device of Example 15, wherein the seal lumens of the first and second seals, when in a non-compressed state, form a circular cross-section and, when compressed, expand radially inwardly to form a non-circular cross-section.

In Example 17, the vascular introducer device of Example 15, wherein the seal lumens of the first and second seals, when compressed, expand radially inwardly to form a smaller lumen diameter configured for providing a fluid-tight seal around a device that has a non-circular cross-section.

In Example 18, the vascular introducer device of Example 15, wherein an inner diameter of the first seal lumen, when the seal is in a non-compressed state, is larger than the inner diameter of the second seal lumen, when the second seal in a non-compressed state.

In Example 19, a method of introducing a catheter into a patient includes obtaining an introducer, inserting the introducer into a patient's vasculature, and inserting a catheter into the introducer. The inserting step includes opening a proximal seal of an introducer hub by rotating a proximal actuator of the introducer hub; inserting the catheter into a proximal end of the introducer hub; advancing the catheter into a lumen of the introducer hub; closing the proximal seal over the catheter such that the catheter is slidably moveable through the proximal seal and bodily fluids are substantially contained within the lumen of the hub by the proximal seal; and opening a distal seal by rotating a distal actuator and advancing the catheter through the distal seal.

In Example 20, the method of Example 19, further including closing the distal seal such that the catheter is positionally locked by the distal seal, thus no longer slidably moveable through the proximal seal.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 2A and 2B are an end view of an introducer hub of the introducer shown in FIG. 1. FIG. 2A shows the introducer hub in a closed state and FIG. 2B shows the introducer hub in an open state.

FIGS. 3A-3C illustrate a method of passing a catheter through the introducer hub of FIG. 1. FIG. 3A shows a catheter being advanced towards a proximal end of the introducer hub. FIG. 3B shows the catheter being inserted into a chamber between the proximal end and a distal end of the hub. FIG. 3C shows the catheter extended through the distal end of the hub.

FIGS. 4A-4E are various views of an alternative embodiment of an introducer hub. FIGS. 4A and 4B are perspective and side views, respectively, of the hub.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
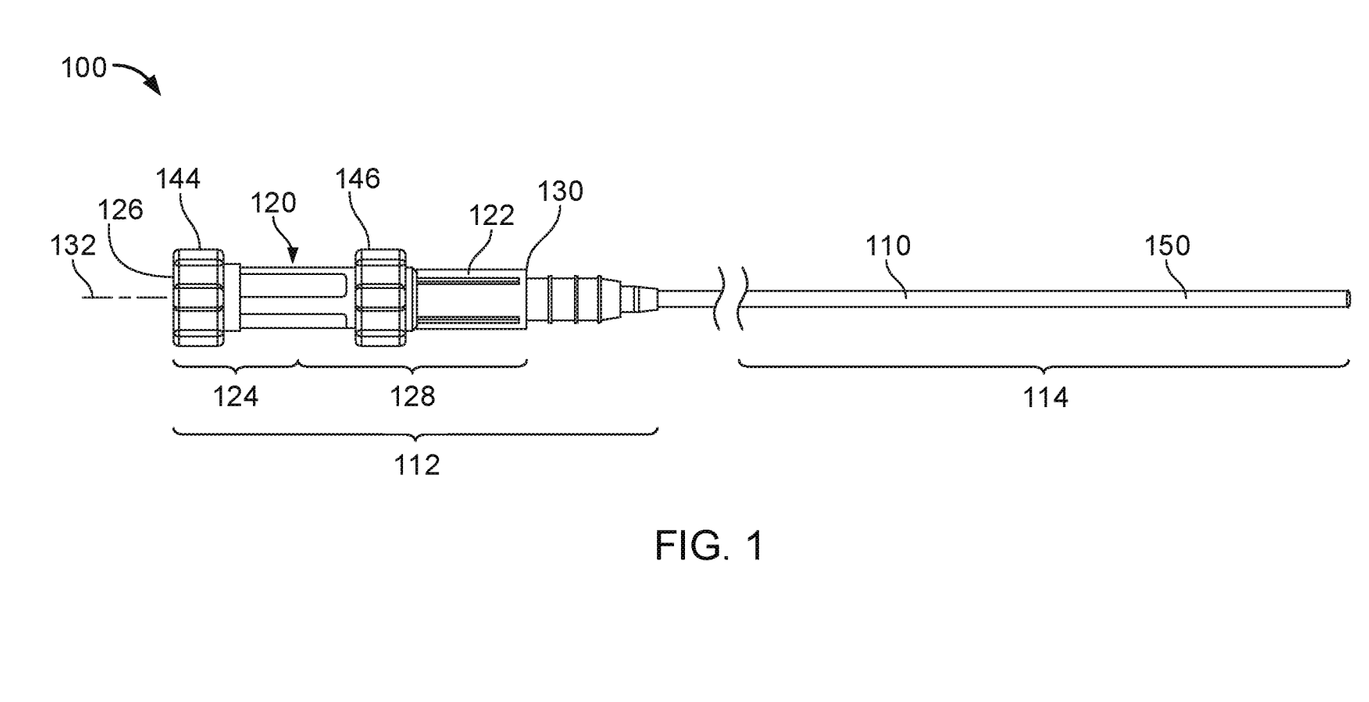
FIG. 1 is a side view of an exemplary introducer provided herein.

Referring to FIG. 1, a vascular introducer 100 according to some cases provided herein has an elongate body 110 extending from a proximal portion 112 to a distal portion 114. The introducer can provide a pathway for a second device, such as a surgical device or a diagnostic device (not shown), through at least a portion of a patient's vasculature, such as a blood vessel (e.g., superior or inferior vena cava) that leads to a heart. In various cases provided herein, the introducer 100 can be configured for providing a pathway for a visualization device (e.g., device 160 in FIGS. 3A-3C) through a patient's vasculature to the heart. For example, in some cases, the introducer 100 can provide a pathway for a balloon-based visualization device through a patient's vasculature from the jugular vein to the superior jugular vein, or from a femoral vein to the inferior vena cava, to the right atrium. The introducer 100, in some cases, can be part of a direct visualization system configured for a tricuspid heart valve repair or replacement procedure. Certain embodiments of the introducer provided herein can be used in medical procedures that treat other areas of a body, for example, the peripheral or cerebral vasculature.

As shown in FIG. 1, the proximal portion 112 of the introducer 100 provided herein includes a hub assembly 120 configured for receiving a second device (e.g., a visualization device) such that the second device can slidably move therein with a small amount of blood leakage, or, alternatively, no blood leakage from the hub assembly 120. The depicted hub assembly 120 includes a body 122, such as a generally cylindrical body, having a proximal portion 124 with a proximal end 126 and a distal portion 128 with a distal end 130. The depicted body 122 defines a longitudinal axis 132 and a lumen (see lumen 139 of FIGS. 2A and 3B) extending from the proximal end 126 to the distal end 130. As will be discussed in greater detail later, the introducer 100 provided herein includes a hub assembly 120 with a proximal actuator 144 (which can also be described as a proximal fitting), a proximal seal 138 (see FIGS. 2A and 2B), a distal actuator 146 (or distal fitting), and a distal seal (not shown). The introducer hub assembly 120 provided herein, in some cases, includes at least one or more seals 138 configured for releasably and sealably coupling to the second device.

The introducer 100 provided herein includes a shaft member 150 connected to and extending distally from the hub assembly 120. In some cases, the shaft member 150 can be a flexible tube configured for inserting into and partially or fully conform a patient's vasculature such that potential damage to the blood vessels during device insertion or during a medical procedure can be minimized. The shaft member 150 can include a lumen therethrough sized to receive a second device (e.g., a visualization device). In some cases, the shaft member 150 is made of a flexible polymer material that allows the shaft member to flex and fully conform, or partially conform, to a tortuous pathway of a patient's vasculature. Suitable shaft materials include, but are not limited to, polyurethanes, polyethylene terephthalate (PET), poly(ethylene oxide) (PEO) and poly(butylene terephthalate) copolymers (PBT), polyamides, and combinations thereof.

Figure 2A:
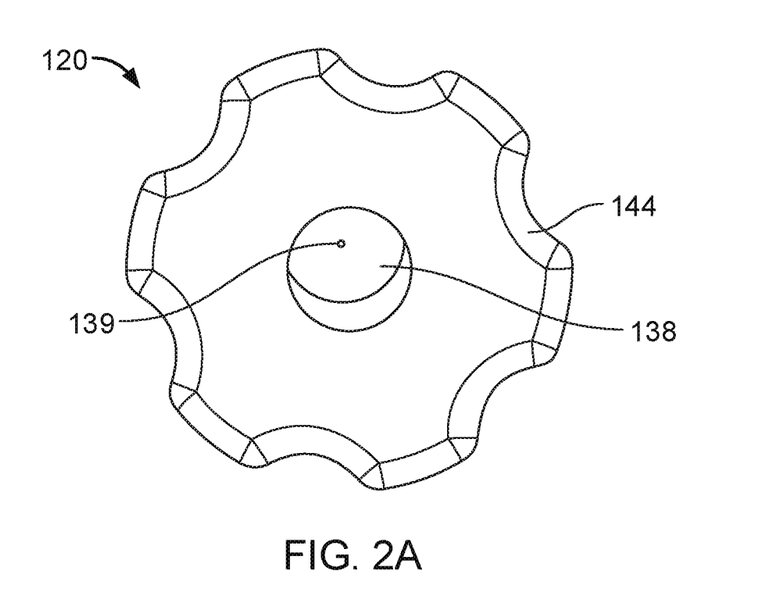
Figure 2B:
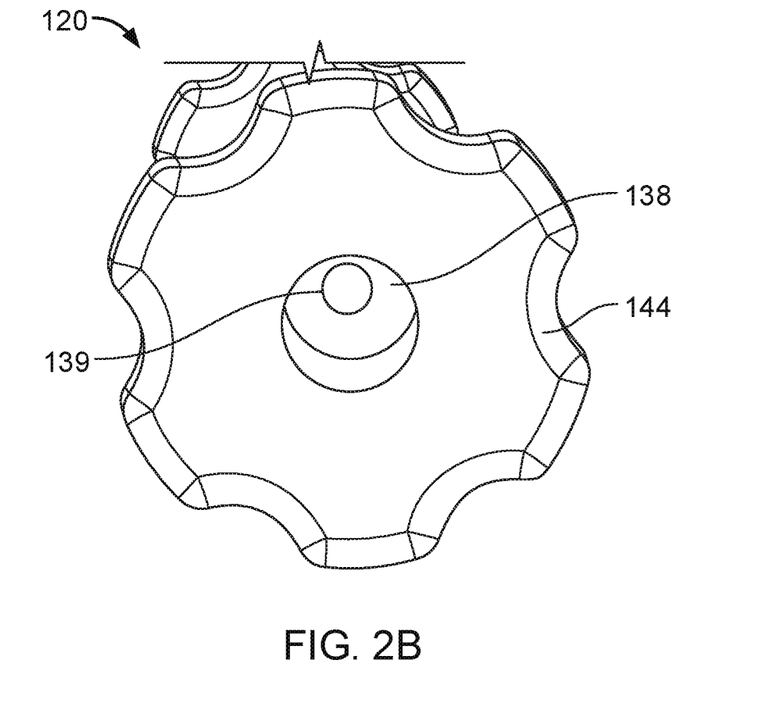

Referring to FIGS. 2A and 2B, in use, the depicted hub assembly 120 has the proximal seal 138 disposed within the body 122 at the proximal portion 124 and the distal seal disposed at the distal portion 128. Each seal can be transition between two states: a closed state (FIG. 2A) and an open state (FIG. 2B). The proximal seal 138 or distal seal of the hub assembly can be adjusted from a closed state to an open state when the seal is axially compressed. There are various ways for axially compressing a hub seal (e.g., the proximal seal 138). In some cases, a rotatable compression nut 144 can be disposed adjacent to a seal (e.g., the proximal seal 138). The rotation of the compression nut 144 can cause the nut 144 to translate distally or proximally along the longitudinal axis defined by the body 122. The longitudinal translation of the nut 144 can axially compress the seal 138 such that the seal material compresses and radially expands inwardly. The radial expansion causes the lumen of the compressed seal to become smaller in size (e.g., diameter) as compared to when the lumen when it is in a non-compressed state. As a result, the lumen (e.g., lumen 139) of a seal (e.g., a proximal seal 138 as shown in FIGS. 2A and 2B), has an adjustable opening that can form a larger diameter when in an open state and smaller diameter when in a closed state, or even no opening when in the closed state (not shown) in certain cases. The lumen (e.g., lumen 139) of the seal (e.g., proximal seal 138), when in an open or partially open state, can allow the passage of a secondary device (e.g., a visualization device) therethrough.

The lumen (e.g., lumen 139) of a fully open seal (e.g., proximal seal 138 as shown in FIG. 2B) can define an opening with a maximum inner diameter. The maximum inner diameter of the opening can be sized as desired. For example, in some cases, the maximum inner diameter can range from about 1 millimeters (mm) to about 10 mm (0.04 inches to about 0.40 inches), e.g., from about 1 mm (0.04 inches) to about 3 mm (0.1 inches), from about 3 mm (0.1 inches) to about 5 mm (0.2 inches), from about 5 mm (0.2 inches) to about 7 mm (0.3 inches), or from about 7 mm (0.3 inches) to about 10 mm (0.4 inches). The lumen of a closed seal defines an opening with a minimum inner diameter. The minimum inner diameter of the opening can be sized as desired. For example, in some cases, the minimum inner diameter can range from about 0.1 mm (0.004 inches) to about 5 mm (0.20 inches), e.g., from about 0.1 mm to about 0.5 mm, from about 0.5 mm to about 1 mm, from about 1 mm to about 2 mm, from about 2 mm to about 3 mm, from about 3 mm to about 4 mm, or from about 4 mm to about 5 mm. In some cases, the minimum inner diameter can be less than 0.1 mm (0.004 inches). In various embodiments, the minimum inner diameter is a smaller dimension than the maximum inner diameter, for example, the minimum inner diameter can range from about 0.5 mm (0.2 inches) to about 9.5 mm (0.4 inches) smaller in diameter as compared to the maximum inner diameter. The inner diameter of the seal opening can be adjusted to an inner diameter size ranging from the minimum seal diameter to the maximum seal diameter.

Figure 3A:
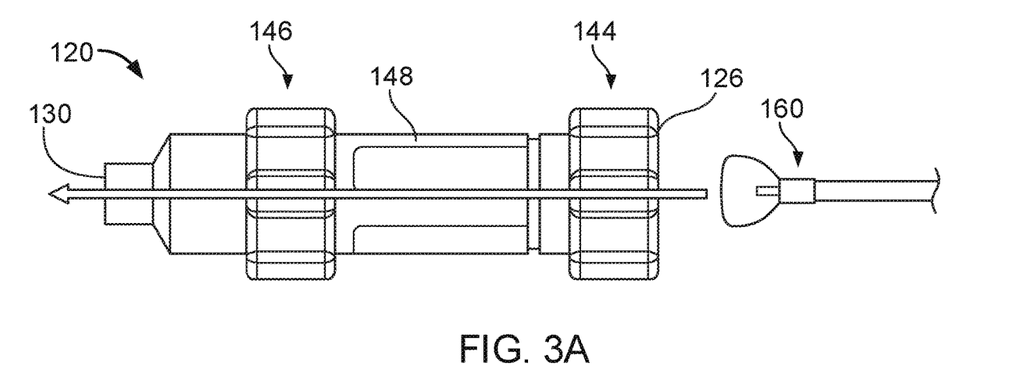
Figure 3B:
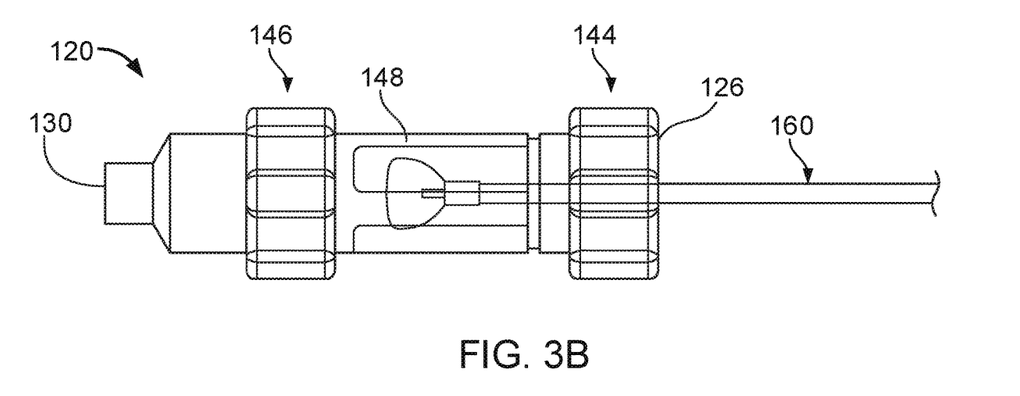
Figure 3C:
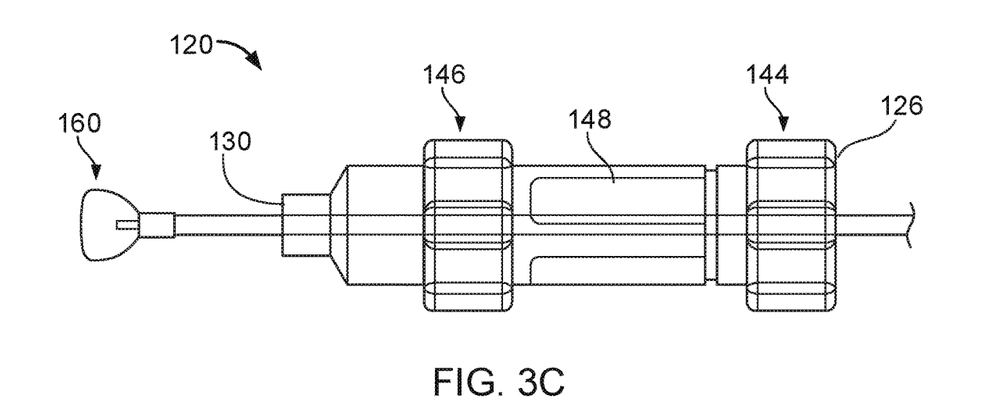

Referring to FIGS. 3A-3C, the exemplary hub assembly 120 of FIG. 1 can be used minimize or prevent blood leakage from the introducer (e.g., introducer 100 of FIG. 1) when introducing a secondary device, such as a balloon-based visualization device 160, into a patient's body. During use, the introducer 100 provided herein (e.g., introducer of FIG. 1) can be introduced into a patient's vascular system, for example, a jugular vein. All of the seals (e.g., proximal seal and distal seals) of the hub assembly 120 may be closed while the introducer 100 is inserted into the patient to prevent blood leakage from the proximal end 126 of the hub assembly 120. Once the introducer 100 has been placed at the desired location within patient's anatomy, the balloon-based visualization device 160 can be advanced (see arrow direction in FIG. 3A) into a lumen at the proximal end 126 of the hub assembly 120. The proximal fitting (e.g., proximal compression nut 144) of the hub assembly 120 can be rotated (e.g., using counter-clock wise rotation) to open the proximal seal of the hub assembly 120. The balloon-based visualization device 160 can be inserted into and through a bore of the proximal seal until the tip of the device 160 is in a chamber portion 148 of the hub assembly 120. The chamber portion 148 of the hub assembly is the luminal region of the hub assembly between the proximal and distal seals. The proximal seal 138 can be tightened by rotating the proximal compression nut 144 (e.g., by clock-wise rotation) such that the proximal seal 138 forms a fluid tight seal around a shaft of the balloon visualization device 160 while still allowing the shaft portion of the device to slidably move distally or proximally along to a longitudinal axis defined by the body 122.

Once the proximal seal has been adjusted to form a fluid tight seal, the distal fitting (e.g., the distal compression nut 146) of the hub assembly 120 can be actuated (e.g, rotated counter-clock wise) to open the distal seal, allowing blood from the patient to flow into the hub chamber portion 148. As shown in FIG. 3C, the balloon visualization device 160 is advanced in a distal direction until the balloon portion of the device 160 passes through the distal seal. The distal seal may be optionally tightened by rotating the distal fitting (e.g., using clock-wise rotation) such that the distal seal forms a fluid tight seal around the shaft of the balloon visualization device 160 while still allowing the shaft to slidably move distally or proximally along a longitudinal axis defined by the body 122 such that a practitioner can, for example, pass the device 160 through the patient's vasculature and reach a heart chamber, such as the right atrium. Optionally, the practitioner may tighten the proximal fitting, distal fitting, or both, when the balloon visualization device 160 has been properly placed within the patient's anatomy to prevent the device 160 from moving distally or proximally along a longitudinal axis defined by the body 122, to stabilize the location of the visualization device 160 within the patient.

Figure 4A:
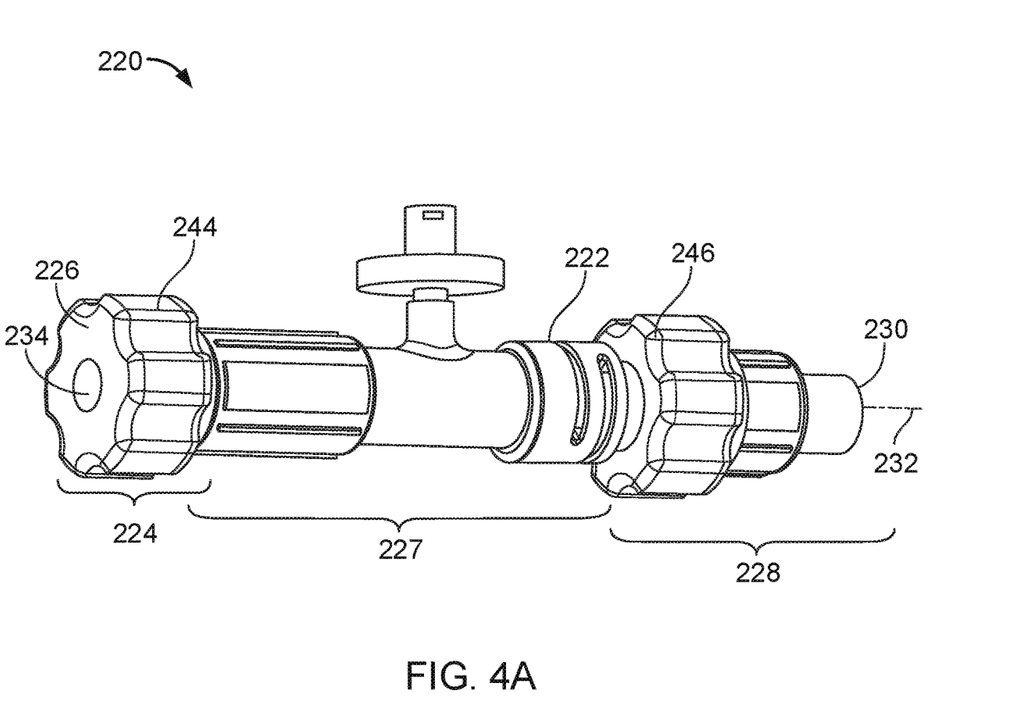
Figure 4B:
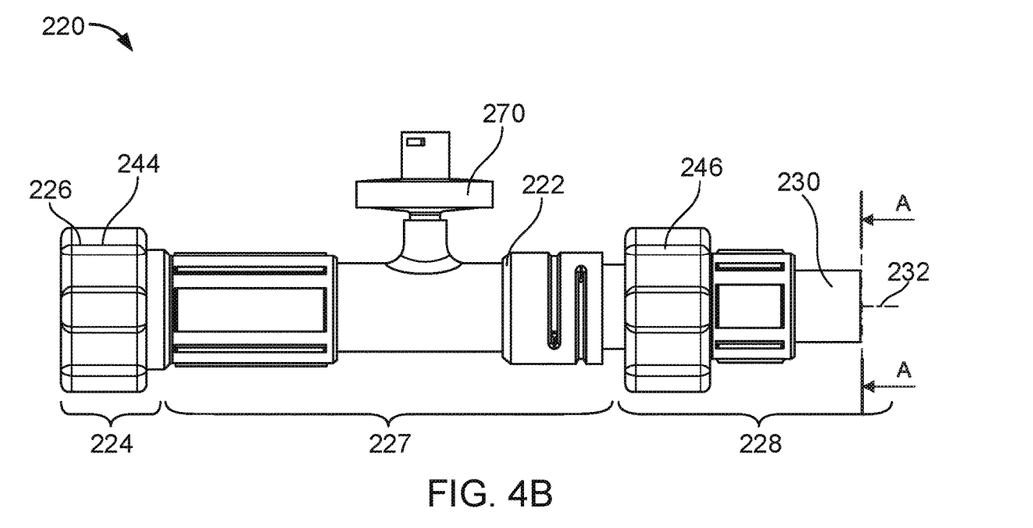
Figure 4C:
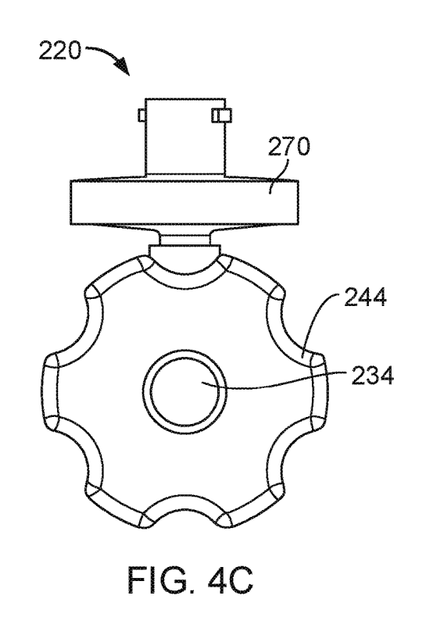
FIGS. 4C and 4D are front and back views, respectively, of the hub.
Figure 4D:
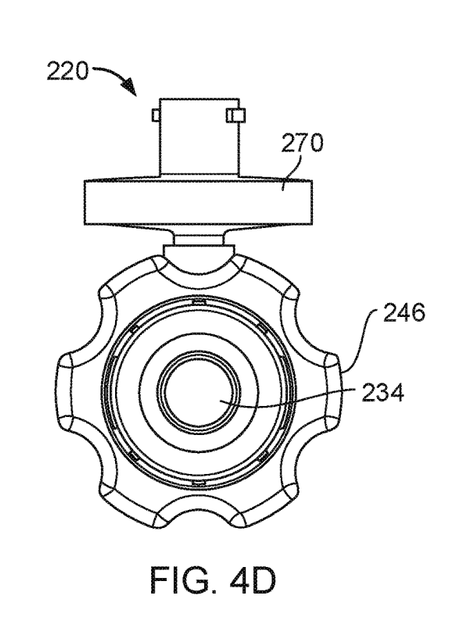
Figure 4E:
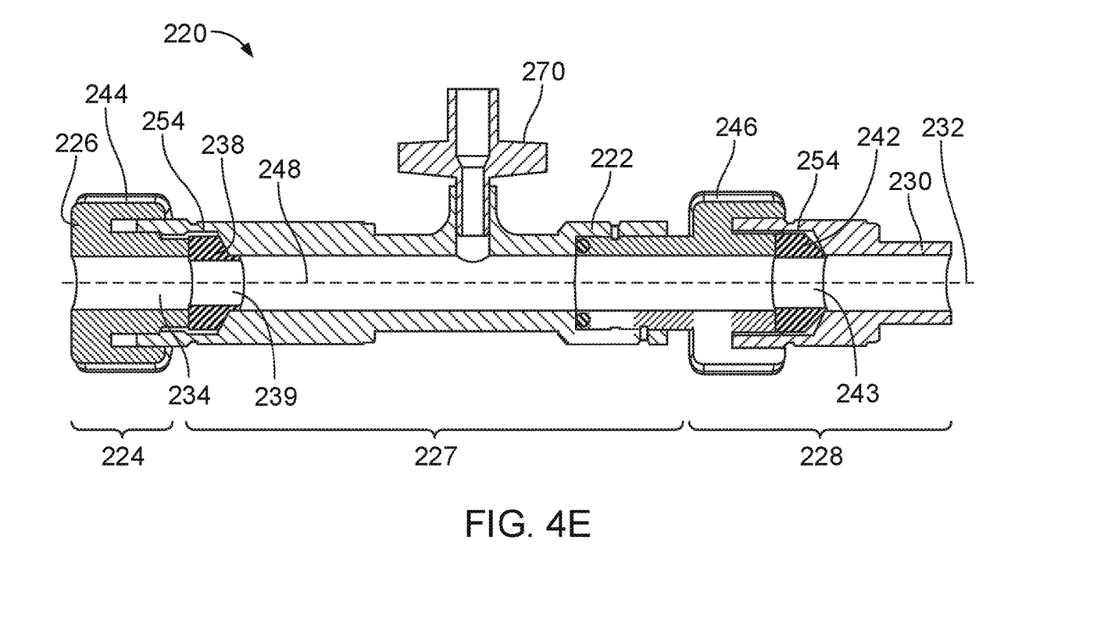
FIG. 4E is a cross-sectional side view of the hub at section A-A.

Referring to FIGS. 4A-4E, another exemplary introducer provided herein includes a hub assembly 220 that has includes a body 222 with a proximal portion 224, middle portion 227, and a distal portion 228. Note that FIGS. 4A-4E are simplified illustrations showing only the hub assembly 220 of the introducer and therefore do not show a shaft portion of the introducer, such as the shaft 150 of FIG. 1. FIGS. 4A and 4B are perspective and side views, respectively, and FIGS. 4C and 4D are front and back views, respectively, of the hub assembly. FIG. 4E provides a cross-sectional view of the hub assembly at section A-A.

The hub 220 of the introducer provided herein can be configured for receiving a second device (e.g., a visualization device) and allowing the second device to slidably move therein with a low amount of blood leakage, or even no blood leakage, from the hub. The depicted hub 220 includes an elongate body 222 defining a longitudinal axis 232 and a lumen 234 (best shown in FIGS. 4D-4E) that extends from a proximal end 226 to a distal end 230 of the body 222. The hub 220, as depicted in FIGS. 4A-4E, also includes a proximal fitting (e.g., a proximal compression nut 244) at the proximal portion and a distal fitting (e.g., a distal compression nut 246) at the distal portion 228. The proximal and distal fittings are configured for adjusting proximal and distal seals 238, 242 (FIG. 4E), respectively, within the hub 220. The depicted introducer hub 220 also includes a venting element 270 in the middle portion 227 of the body 222 for releasing gas from within the interior areas, such as a chamber portion 248 of the hub 220 (see FIG. 4E).

Still referring to FIGS. 4A-4E, the hub 220 can include two or more fittings (e.g., the proximal and distal compressional nuts 244, 246) to facilitate adjustment of the seals. In some cases, the hub 220 can include more than two fittings and seals, for example, three, four, five, or more than five fittings and seals. The proximal and distal fittings, as shown in FIGS. 4A-4E, can each be movably coupled to the body 222 of the hub 220. Each fittings can be a rotatable fitting, for example, a compression nut, configured for compressing the seals when rotated. Each fittings can increase or decrease the compressive force exerted on the each corresponding seal depending on a number of rotational turns. In some case, when rotated, a portion of each fitting can reciprocate between a first position and a second position along the longitudinal axis within the hub. The distance between the first and second positions creates a compressional force in the axial direction that is directly applied by the fitting to the adjacent seal, for example, from the proximal fitting to the proximal seal 238. In various cases, each fitting can exert or remove a compressional force applied to the seal such that the seal is able to close, open, or partially open, about the circumference of a secondary device (e.g., visualization device) in response to the exertion or removal of the force.

The introducer hub provided herein can include at least two seals, for example, the proximal and distal seals 238, 242, which are best shown in FIG. 4E. Each seal (e.g., the proximal seal 238) can be disposed within an annular cavity 254 of the hub located between one of the fittings and the middle portion 227 of the hub 220. Each seal includes a body defining a lumen 239, 243 therethrough for providing a fluid conduit within the hub 220. The seal body can be formed in various different forms that include, but are not limited to, a generally cylindrical body, a flat or elliptical ring, or an o-ring shaped body. In some cases, as shown best in FIG. 4E, the proximal and distal seals 238, 242 each have a cylindrical-shaped proximal portion and a frustoconical-shaped distal portion. The frustoconical-shaped distal portion allows the seal to circumferentially expand under less compressional force as compared to the cylindrical-shaped proximal portion of the seal when the seal is subjected to compressional force. In some cases, the frustoconical-shaped distal portion puckers radially inward when the seal is compressed.

In various cases, the seal (e.g., the proximal and/or distal seals 238, 242) of the introducer hub provided herein responds to compressive forces exerted thereon to provide a fluid-tight seal over a secondary device (e.g., a visualization device). When compressive force is exerted on the seal, a portion of seal (e.g., the frustoconical-shaped distal portion) moves radially inward to form a progressively tighter seal around the secondary device, such as a visualization device, disposed in the lumen of the seal. The amount of compressive force being exerted on each seal can be incrementally adjusted so that a fluid-tight seal is formed or maintained around the shaft of a visualization device while still allowing the device to be repositioned, or even removed without having to remove all of the compressive force acting on the compressible seal. This adjustable characteristic of seal is adapted for receiving elongate medical devices having a variety of different diameters and cross-sectional shapes therethrough.

In some cases, the seal of the introducer hub can include a body defining a lumen with various cross-sectional shapes. Some cross-sectional shapes include, but are not limited to, a circular, oval, and various polygonal shapes.

The seal can be made of various polymeric materials. In some cases, the seal can be made of a resilient material adapted for elastically deforming under compression force, and returning back to its original shape when the force is removed. Suitable materials for the seal can include, but are not limited to, an elastomer such as a silicone rubber.

In some cases, the introducer hub provided herein includes at least two seals, a first seal and a second seal. The first seal can contain a first material and a second seal can contain a second material, in which the first and second materials have different mechanical properties. In some cases, the first and second materials can includes materials of the same polymer class that has different mechanical properties, such as different durometers. For example, the proximal seal can be made of a first polymeric material, such as a low durometer silicone, and the distal seal can be made of a second polymeric material, such as a high durometer silicone. A low durometer silicone is a silicone having a durometer ranging from a 10 Shore A durometer to about a 40 Shore A durometer and a high durometer silicone is a silicone having a durometer ranging from about a 40 Shore A durometer to a 60 Shore A durometer. For example, in some cases, the first seal includes a silicone having a durometer ranging from about 30 Shore A to about 40 Shore A and the second seal includes a silicone material having a durometer ranging from about 40 Shore A to about 60 Shore A. In some examples, the first seal that includes a material that has a durometer of about 30 Shore A, and a second seal that includes a material that has a durometer of about 60 Shore A. In some cases, the first and the second materials can be different materials. For example, in some cases, the first seal can include a silicone and the second seal can include a urethane, or a polyurethane blend. In some cases, one of the seal can include a first material associated with a higher or lower stiffness, or elasticity, when compared to a second material of the other seal. The difference in durometer of the first and second seals provide the benefit of allowing one seal (e.g., the first seal, or alternatively, the second seal), made of a higher durometer material, that, when closed, prevents repositioning of the device disposed within the seal while the other seal, made of a lower durometer material, that, when closed, allows for device repositioning, but prevent bodily fluids from leaking from the hub. In sum, the introducer hub provided herein can be configured to be multifunctional, that is, allow devices disposed within the hub to be sealed with a softer, pliable seal to prevent blood leakage while still allowing repositioning of the device, when desired, but also allow devices to be secured to prevent device displacement during a medical procedure, when desired, with a tougher, stiffer seal.

In some cases, the first seal can be configured for forming a fluid-tight seal around a device disposed within the first lumen when the first seal is compressed. In some cases, the first seal can be configured to allow the device to move distally or proximally along a longitudinal axis defined by the hub body when the first seal is in a partially closed state. The first seal can be configured, in certain cases, to allow the device to move distally or proximally along a longitudinal axis defined by the body when first seal is in a fully closed state.

The second seal can be configured, in some cases, to form a fluid-tight seal around a device when the second seal is compressed partially, or fully. In some cases, the second seal can be configured to prevent the device to move distally or proximally along a longitudinal axis defined by the hub body when the second seal is in a partially or fully closed state.

Still referring to FIG. 4E, in some cases, the seal, when in a non-compressed state, can have a longitudinal length of about 0.5 mm (0.02 inches) to about 5 mm (0.20 inches), including all values and ranges therebetween, e.g., from about 0.5 mm to about 1 mm, from about 1 mm to about 2 mm, from about 2 mm to about 3 mm, from about 3 mm to about 4 mm, or from about 4 mm to about 5 mm. The radial width (e.g., diameter) of the seal in a non-compressed state can range from about 1 mm (0.04 inches) to about 5 mm (0.20 inches), including all values and ranges therebetween, e.g., from about 1 mm to about 2 mm, from about 2 mm to about 3 mm, from about 3 mm to about 4 mm, or from about 4 mm to about 5 mm. The thickness of the seal (e.g., the distance between the luminal wall to the nearest exterior wall of the seal) in the non-compressed state can range from about 1 mm (0.04 inches) to about 3 mm (0.12 inches), including all values and ranges therebetween, e.g., about 1 mm to about 1.5 mm, from about 1.5 mm to about 2 mm, from about 2 mm to about 2.5 mm, or from about 2.5 mm to about 3 mm. The lumen of the seal, when in a non-compressed state, can be sized to allow a secondary device having a diameter ranging from about 2.7 mm (0.105 inches; 8 French) to about 8.7 mm (0.341 inches; 26 French) to pass therethrough. For example, in some cases, the lumen of the seal can be sized to allow a secondary device having a diameter ranging of about 2.7 mm to about 4 mm, from about 4 mm to about 6 mm, or from about 6 mm to about 8.7 mm Referring back to FIGS. 4A-4E, the introducer hub provided herein includes a venting element 270 (which can also be referred to as a degassing vent) in the middle portion 227 of the hub body 222 that is adapted for removing gas such as air from within the chamber portion 248 of the hub 220, while leaving liquids such as blood behind. The depicted venting element 270 includes a stem, a mid-portion, and an end portion. The venting element 270 can extends in a direction that is orthogonal or oblique to the longitudinal axis of the hub such that a practitioner can orient the venting element at an elevated height relative to the lumen of the hub 220. The elevated height can provide the benefit of directing gases (e.g., air) from the luminal regions of the hub to the venting element.

The stem of the venting element 270 can be sized to facilitate coupling (e.g., bonding) with the body 222 of the hub 220. For example, the stem can be tapered for press fit connection with a bore defined along the middle portion 227 of the hub 220, as shown in FIG. 4E. In some cases, the end portion of the venting element 270 can include a connector adapted for being operably connected with an outlet line (not shown), such a vacuum line connected to a vacuum source.

The venting element 270 can be shaped to house a gas permeable filter. For example, as shown in FIGS. 4A-4E, the mid-portion of the venting element 270 can be disk-shaped for housing flat filter disks. In some cases, the gas permeable filter made of a porous or microporous membrane made of materials such as, but not limited to, polypropylene, polyethylene, polytetrafluoroethylene, other polyolefin, polyester, or combinations thereof. In some cases, the filter can be made of a hydrophobic material or include a hydrophobic coating. The membrane can include porous structures that extend from one side of the membrane to the other side. The size of the pores can be about 0.004 inches (100 microns) with a range of about 0.002 inches (50 microns) to about 0.040 inches (1000 microns). The pore density and pore size can be selected to be compatible with a pressure drop across the membrane, as generated by a pump or other suction (vacuum) or pressure generating device, so as to remove a given volume of air, while preventing the loss of blood or other liquids from the hub 220.

The introducer hub assembly provided herein can be made using various manufacturing processes. For example, in some cases, discrete components of the introducer hub assembly can be made using processes that include, but are not limited to, extrusion and injection molding. The components of the introducer hub assembly provided herein can be assembled together using manufacturing processes such as adhesive bonding, over-molding, and press or snap-fitting.

It should be understood that one or more design features of the introducer hub assembly provided herein can be combined with other features of other introducer hub provided herein. In effect, hybrid designs that combine various features from two or more of the introducer hub designs provided herein can be created, and are within the scope of this disclosure.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein. All references, publications, and patents referred to herein, including the figures and drawings included therewith, are incorporated by reference in their entirety.

We claim:
1. A vascular introducer hub comprising:
   a body that includes a proximal end, a distal end, and a lumen defined therethrough; and first and second seals disposed within the body, an entirety of the first seal comprising a first polymeric material, and an entirety of the second seal comprising a second polymeric material;

the first and second polymeric materials have different durometers;

wherein the first seal is configured to allow a device to move distally or proximally along a longitudinal axis defined by the body when the first seal is in a partially compressed state and in a fully compressed state;

wherein the second seal is configured to form a fluid-tight seal around a device when the second seal is compressed partially and prevent a device from moving distally or proximally along the longitudinal axis when the second seal is in a fully compressed state.

2. The vascular introducer hub of claim 1, wherein the first polymeric material has a lower durometer than the second material.

3. The vascular introducer hub of claim 2, wherein the first seal comprises a silicone having a durometer ranging from about 30 Shore A to about 40 Shore A and the second seal comprising a silicone material having a durometer ranging from about 40 Shore A to about 60 Shore A.

4. The vascular introducer hub of claim 1, further comprising a first seal actuator rotatably coupled to the body and located adjacent to the first seal and a second seal actuator rotatably coupled to the body and located adjacent to the second seal, wherein the first seal actuator is configured to compress the first seal when actuated and the second seal actuator is configured to compress the second seal when actuated.

5. The vascular introducer hub of claim 4, wherein the first seal includes a seal body defining a first lumen therethrough with a reduceable inner diameter configured to reduce in diameter when the seal body is compressed by the first seal actuator.

6. The vascular introducer hub of claim 1, wherein a lumen of each of the first and second seals, when each is in a non-compressed state, is sized to receive a catheter device having a diameter ranging from about 2.7 mm (0.105 inches; 8 French) to about 8.7 mm (0.341 inches; 26 French).

7. The vascular introducer hub of claim 1, wherein the body defines a chamber between the first and second seals, the chamber being in fluid communication with the lumen of the body.

8. The vascular introducer hub of claim 7, further comprising a venting element coupled to the body and in fluid communication with the chamber, the venting element configured to release gases from the chamber while leaving liquids in the chamber.

9. The vascular introducer hub of claim 8, wherein the venting element extends in radial direction relative to a longitudinal axis defined by the body.

10. The vascular introducer hub of claim 8, wherein the venting element comprising a gas permeable filter made of a porous or microporous membrane made of a material selected from the group consisting of polypropylene, polyethylene, polytetrafluoroethylene, other polyolefin, polyester, or combinations thereof.

11. A vascular introducer device comprising:
an elongate shaft including a proximal end, a distal end, and a lumen therethrough, the lumen sized to receive a catheter device, the distal end defining an opening configured to allow the catheter device to pass through; and a hub coupled to the proximal end of the elongate shaft, the hub comprising:

a body that includes a proximal end, a distal end, and a lumen defined therethrough; and first and second seals disposed within the body, an entirety of the first seal comprising a first polymeric material, and an entirety of the second seal comprising a second polymeric material;

the first and second polymeric materials of the hub having different durometers;

wherein the first seal is configured to allow a device to move distally or proximally along a longitudinal axis defined by the body when the first seal is in a partially compressed state and in a fully compressed state;

wherein the second seal is configured to form a fluid-tight seal around a device when the second seal is compressed partially and prevent a device from moving distally or proximally along the longitudinal axis when the second seal is in a fully compressed state.

12. The vascular introducer device of claim 11, wherein the first seal defines a first seal lumen and comprises a first seal body that includes a frustoconical distal portion tapered in a distal direction and being configured for puckering inwardly when the first seal is compressed, and wherein the second seal defines a second seal lumen and comprises a second seal body that includes a frustoconical distal portion tapered in a distal direction and being configured for puckering inwardly when the second seal is compressed.

13. The vascular introducer device of claim 12, wherein the seal lumens of the first and second seals, when in a non-compressed state, form a circular cross-section and, when compressed, expand radially inwardly to form a non-circular cross-section.

14. The vascular introducer device of claim 12, wherein the seal lumens of the first and second seals, when compressed, expand radially inwardly to form a smaller lumen diameter configured for providing a fluid-tight seal around a device that has a non-circular cross-section.

15. The vascular introducer device of claim 12, wherein an inner diameter of the first seal lumen, when the seal is in a non-compressed state, is larger than an inner diameter of the second seal lumen, when the second seal in a non-compressed state.

16. A method of introducing a catheter into a patient, the method comprising:
obtaining an introducer;
inserting the introducer into a patient's vasculature;
inserting a catheter into the introducer, the inserting comprising:
opening a proximal seal of an introducer hub by rotating a proximal actuator of the introducer hub;
inserting the catheter into a proximal end of the introducer hub;
advancing the catheter into a lumen of the introducer hub;
closing the proximal seal over the catheter such that the catheter is slidably moveable through the proximal seal and bodily fluids are substantially contained within the lumen of the hub by the proximal seal; and
opening a distal seal by rotating a distal actuator and advancing the catheter through the distal seal;

wherein an entirety of the proximal seal comprises a first polymeric material and an entirety of the distal seal comprises a second polymeric material, wherein the first and second polymeric materials have different durometers;

wherein the proximal seal is configured to allow a device to move distally or proximally along a longitudinal axis defined by the body when the proximal seal is in a partially compressed state and in a fully compressed and closed state;

wherein the distal seal is configured to form a fluid-tight seal around a device when the distal seal is compressed partially and prevent a device from moving distally or proximally along the longitudinal axis when the distal seal is in a fully compressed and closed state.

17. The method of claim 16, further comprising closing the distal seal such that the catheter is positionally locked by the distal seal, thus no longer slidably moveable through the proximal seal.

\* \* \* \* \*